United States Patent
Colombo et al.

(10) Patent No.: US 6,520,988 B1
(45) Date of Patent: Feb. 18, 2003

(54) ENDOLUMENAL PROSTHESIS AND METHOD OF USE IN BIFURCATION REGIONS OF BODY LUMENS

(75) Inventors: Antonio Colombo, Milan (IT); Robert D. Lashinski, Sebastopol, CA (US); Matthew J. Birdsall, Santa Rosa, CA (US); Dennis L. Brooks, Windsor, CA (US); Philip J. Haarstad, Santa Rosa, CA (US); James C. Peacock, III, Sunnyvale, CA (US)

(73) Assignee: Medtronic AVE, Inc., Santa Rosa, CA (US)

( * ) Notice: Subject to any disclaimer, the term of this patent is extended or adjusted under 35 U.S.C. 154(b) by 0 days.

(21) Appl. No.: 08/937,130

(22) Filed: Sep. 24, 1997

(51) Int. Cl.$^7$ .................................................. A61F 2/06
(52) U.S. Cl. ...................... 623/1.35; 623/1.11; 623/1.27
(58) Field of Search ............................ 623/1, 12, 1.16, 623/1.27, 1.11, 1.35; 606/108, 192, 194, 195

(56) References Cited

U.S. PATENT DOCUMENTS

| | | | |
|---|---|---|---|
| 4,580,568 A | 4/1986 | Gianturco | 128/345 |
| 4,733,665 A | 3/1988 | Palmaz | 128/343 |
| 4,739,762 A | 4/1988 | Palmaz | 128/343 |
| 4,776,337 A | 10/1988 | Palmaz | 128/343 |
| 4,830,003 A | 5/1989 | Wolff | 128/343 |
| 4,913,141 A | 4/1990 | Hillstead | 606/108 |
| 4,969,458 A | 11/1990 | Wiktor | 606/194 |

(List continued on next page.)

FOREIGN PATENT DOCUMENTS

| | | | | |
|---|---|---|---|---|
| EP | 0 804 907 A2 | 5/1997 | | |
| FR | 2678508 | * | 1/1993 | 623/1 |
| WO | 9641592 | * | 12/1996 | 623/1 |
| WO | WO 9819628 | | 5/1998 | |
| WO | WO 9836709 | | 8/1998 | |

OTHER PUBLICATIONS

Foley et al., "Bifurcation Lesion Stenting", The Thoraxcentre Journal, vol. 8, No. 4, Dec. 1996.
Freed, M.D. et al., "The New Manual of Interventional Cardiology", Chapter 10, pp. 238–243, 1996.
Pentachi–Sitomed Srl Advertising Brochure illustrating "SITOSTENT(Registered trademark) S" and "JOSTEN-T(Registered trademark) B".

Primary Examiner—Bruce Snow
(74) Attorney, Agent, or Firm—Catherine C. Maresh

(57) ABSTRACT

An endolumenal medical device assembly is provided for use in a bifurcation region of a body lumen. An expandable prosthesis, such as a stent, is included in the assembly and is adjustable from a radially collapsed condition to a radially expanded condition. The expandable prosthesis includes a prosthesis passageway and a side port. A dilator or an access device is engaged within the prosthesis passageway and also through the side port while the expandable prosthesis is in the radially collapsed condition. The expandable prosthesis may be positioned in the bifurcation region such that its distal end portion is in a first branch lumen extending from the bifurcation, its proximal end portion is in a common proximal lumen of the bifurcation region, and the side port is aligned with an entrance zone to a second branch lumen extending from the bifurcation. When the expandable prosthesis is so positioned the access device maintains percutaneous translumenal access to the second branch lumen through the prosthesis passageway and the side port while the expandable prosthesis is adjusted from the radially collapsed condition to the radially expanded condition. A dilator may also to expand the bore formed by the side port from an initial inner diameter to a larger expanded inner diameter. A second, lateral expandable prosthesis can also be coupled to the first expandable prosthesis at a location adjacent to the side port and engaged by the dilator or access device extending through the side port.

18 Claims, 9 Drawing Sheets

U.S. PATENT DOCUMENTS

| | | | |
|---|---|---|---|
| 4,994,071 A | 2/1991 | MacGregor | 606/194 |
| 5,019,090 A | 5/1991 | Pinchuk | 606/194 |
| 5,292,331 A | 3/1994 | Boneau | 606/198 |
| 5,669,924 A | 9/1997 | Shaknovich | 606/108 |
| 5,718,724 A | 2/1998 | Goicoechea et al. | 623/1 |
| 5,720,735 A | 2/1998 | Dorros | 604/284 |
| 5,723,004 A | 3/1998 | Dereume | 623/1 |
| 5,749,825 A | 5/1998 | Fischell et al. | 600/3 |
| 5,749,848 A | 5/1998 | Jang et al. | 604/53 |
| 5,749,888 A | 5/1998 | Yock | 606/194 |
| 5,755,735 A | 5/1998 | Richter et al. | 606/194 |
| 5,755,771 A | 5/1998 | Penn et al. | 623/1 |
| 5,855,600 A * | 1/1999 | Alt | 623/1 |

* cited by examiner

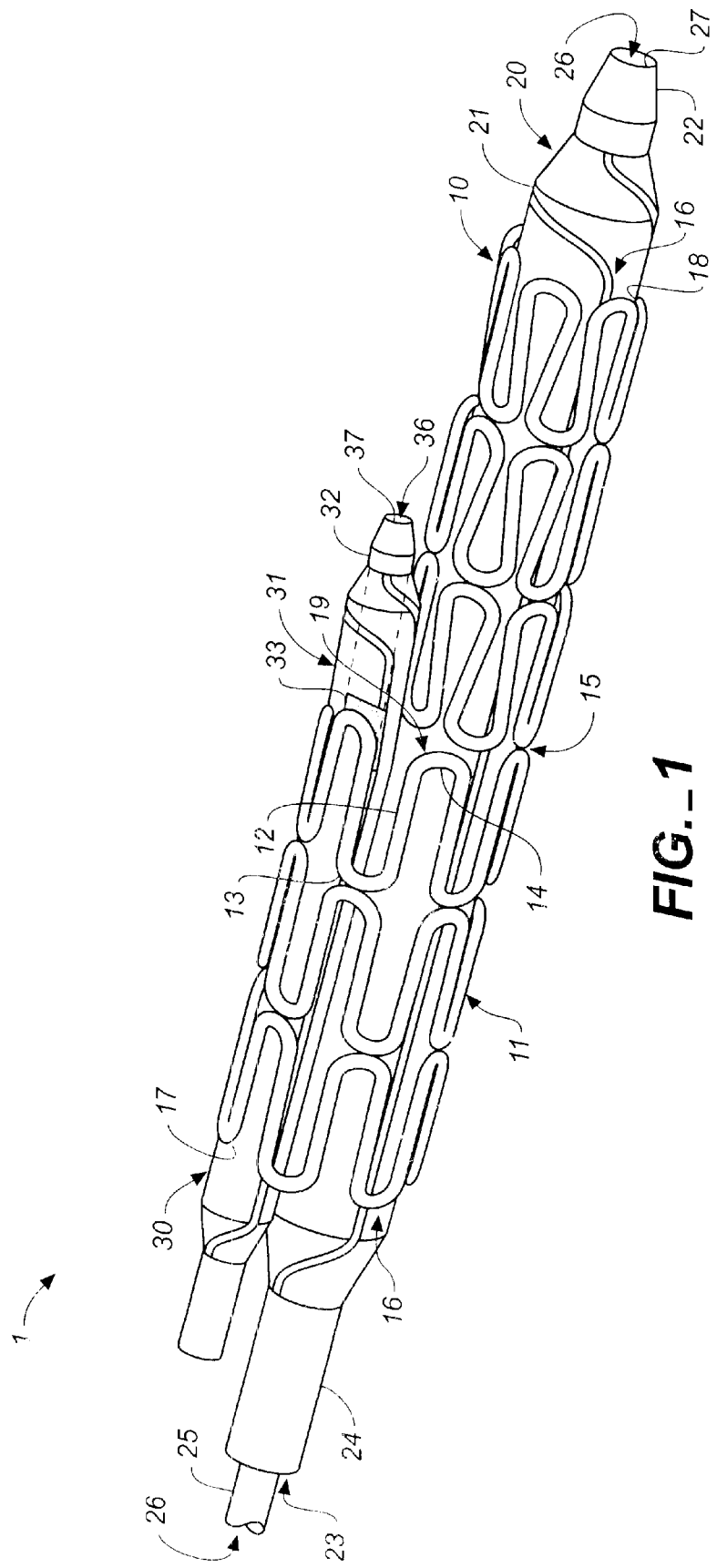
FIG._1

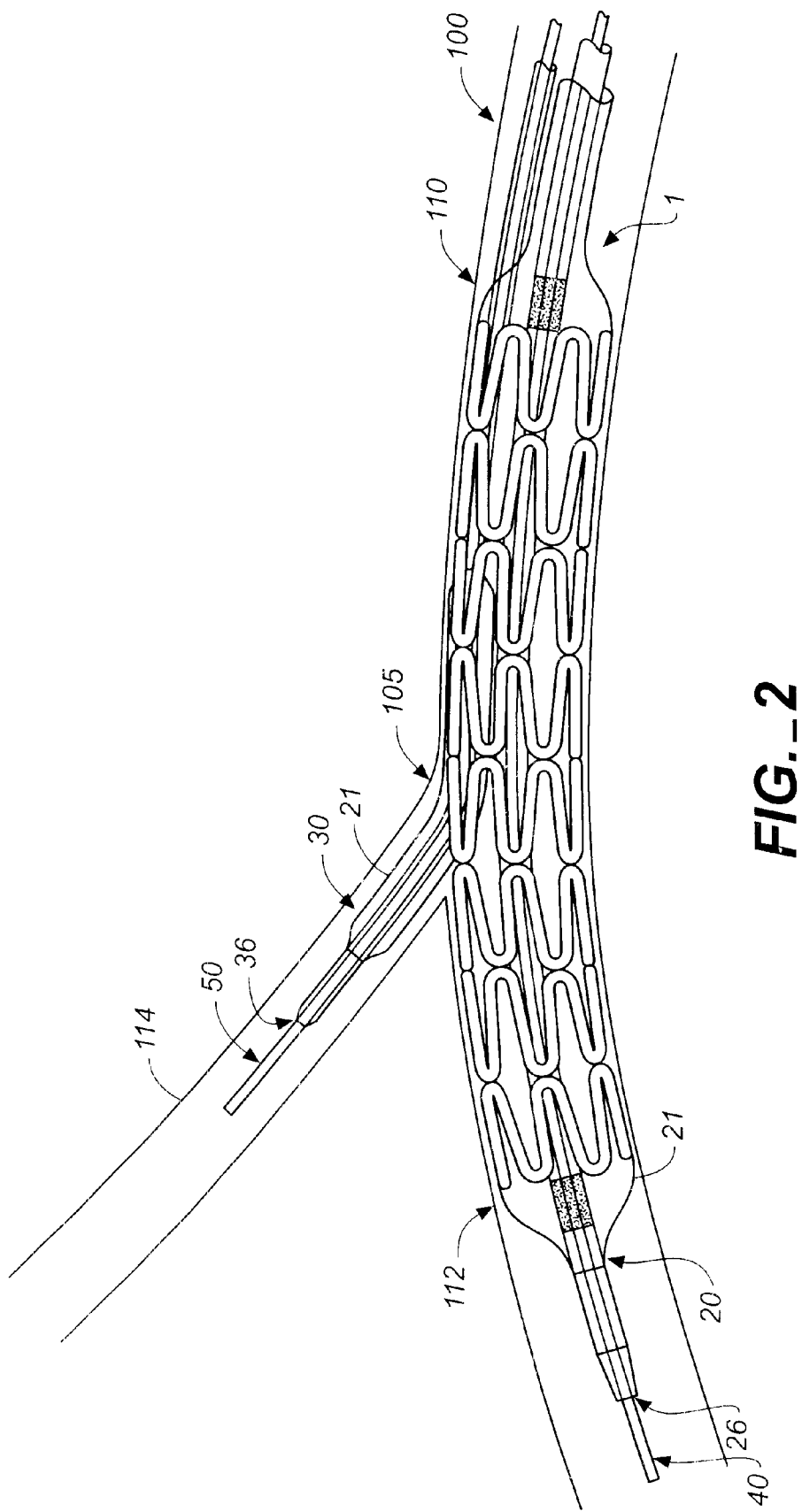
FIG._2

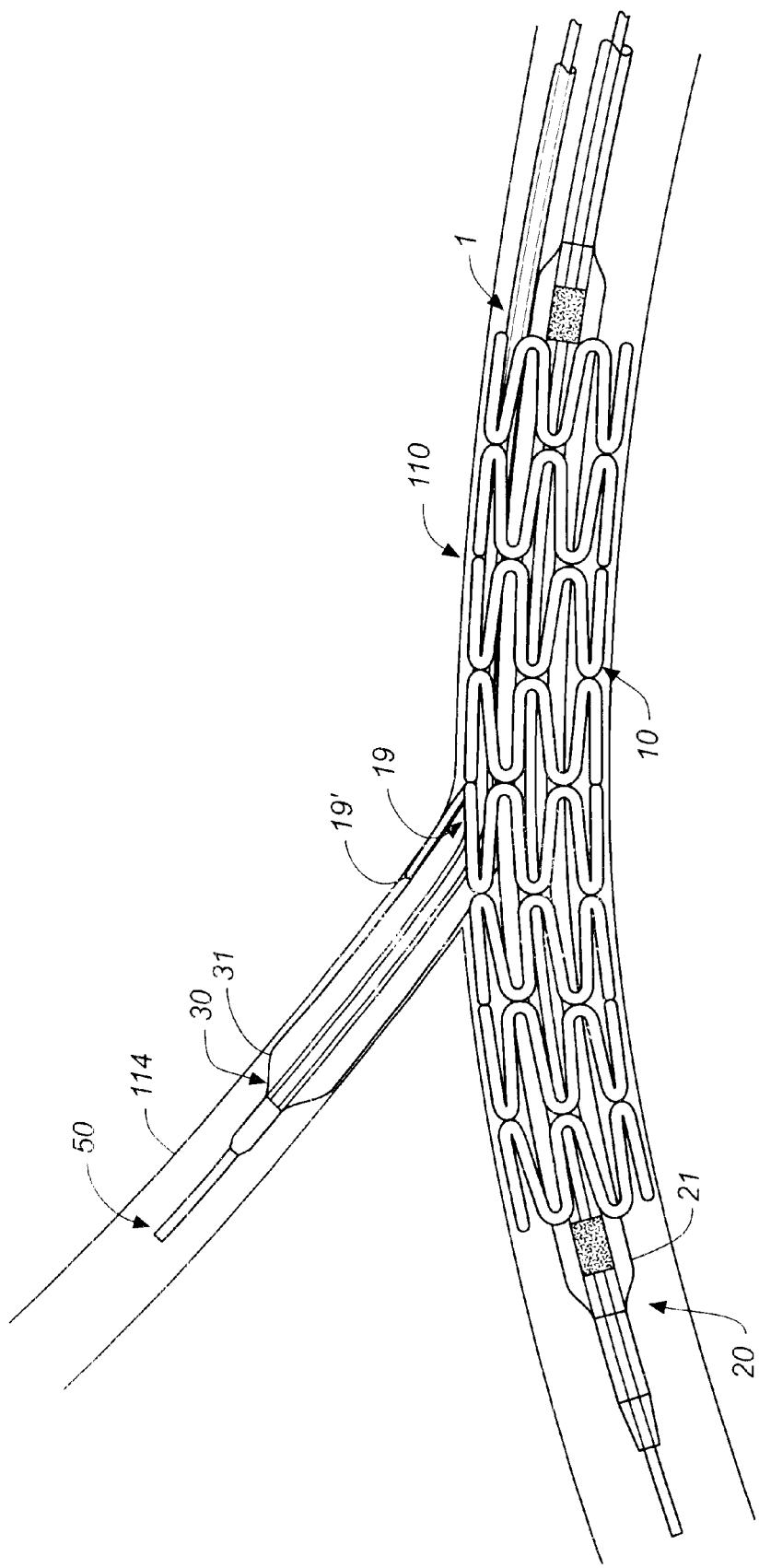
FIG._3

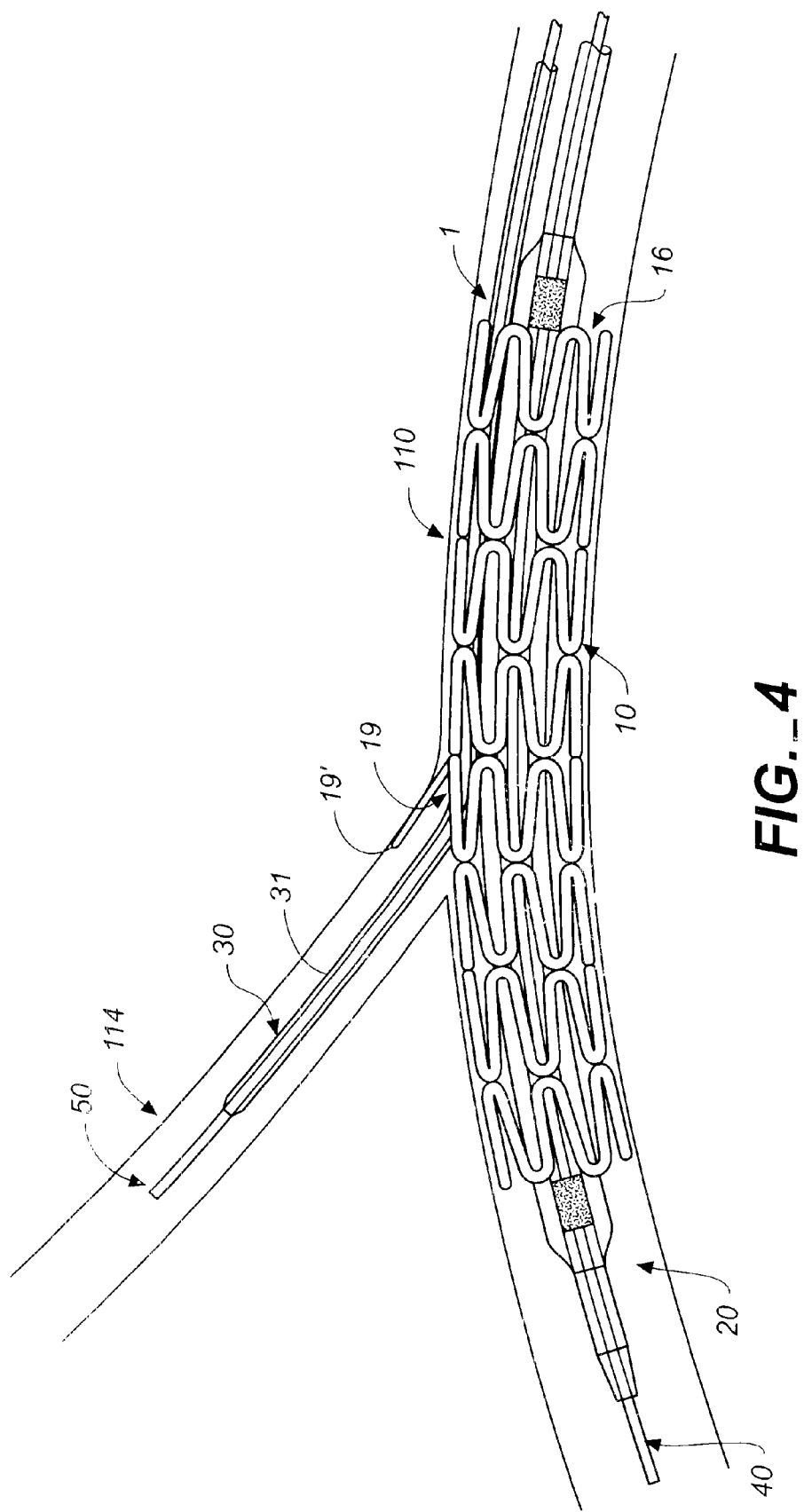
FIG._4

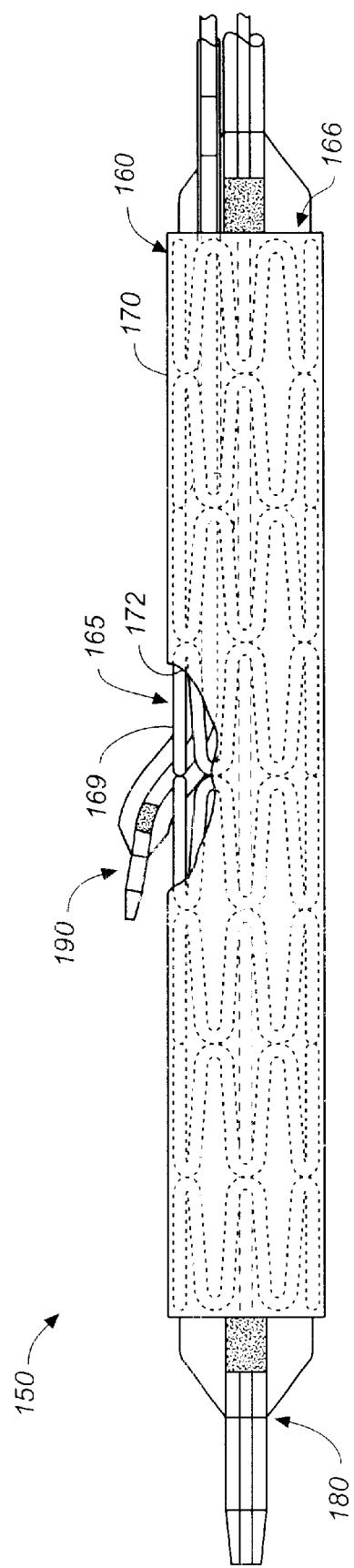
FIG._5

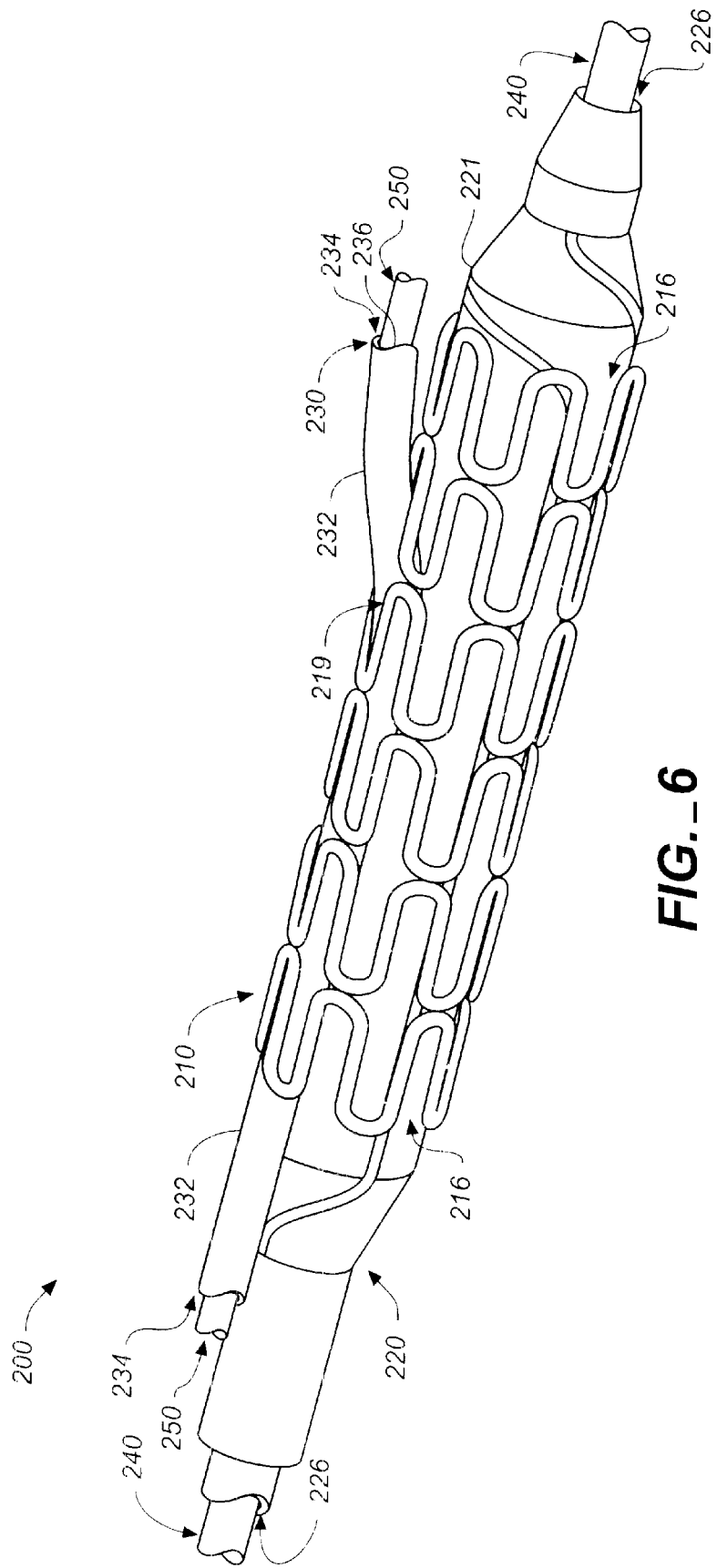

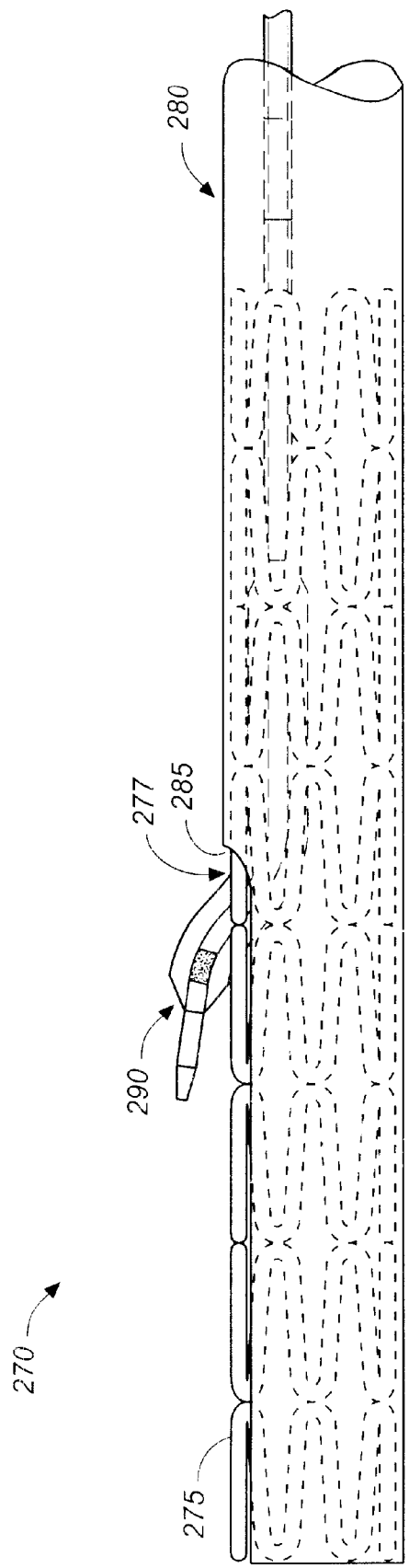
FIG._7

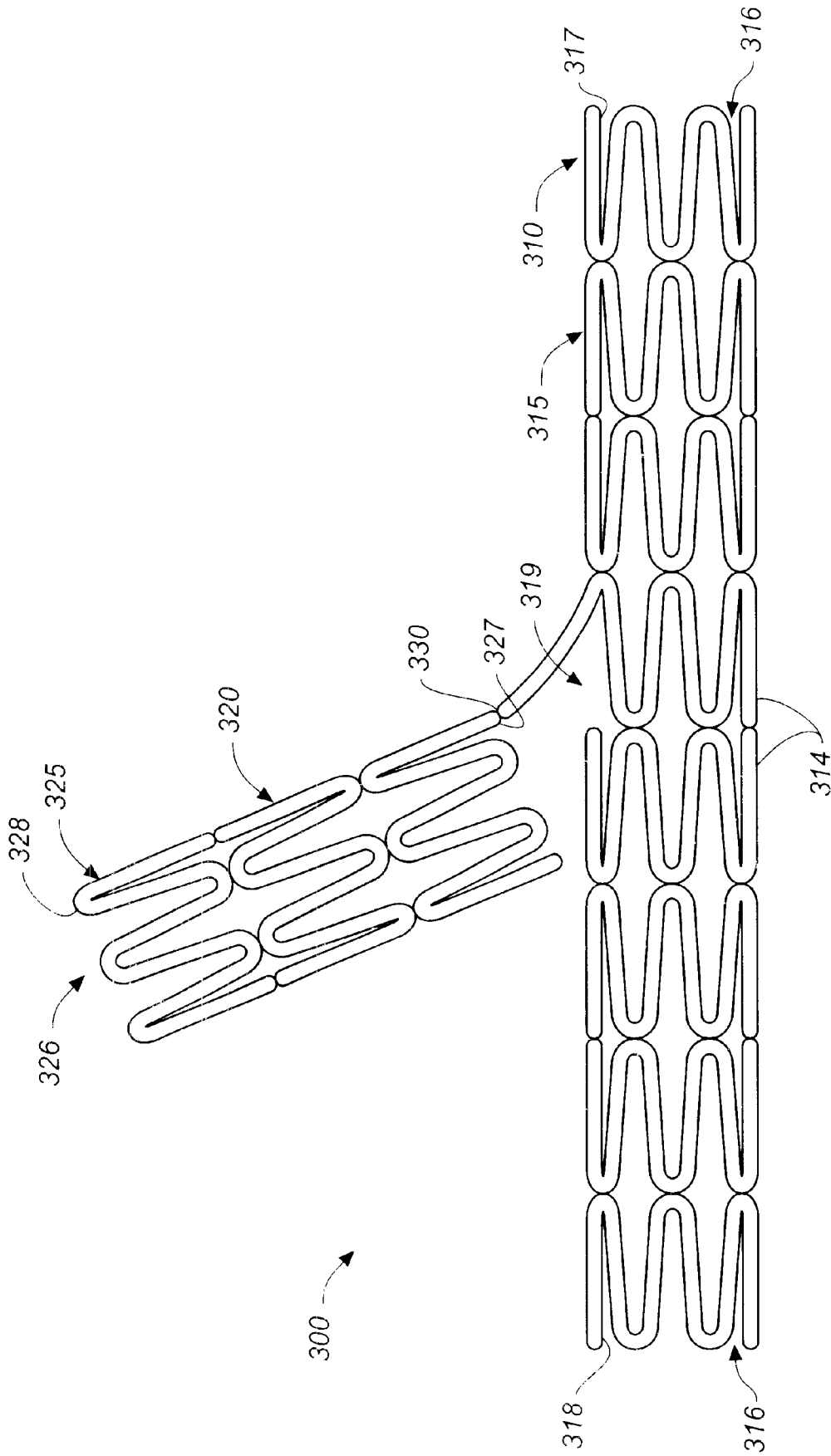
FIG._8A

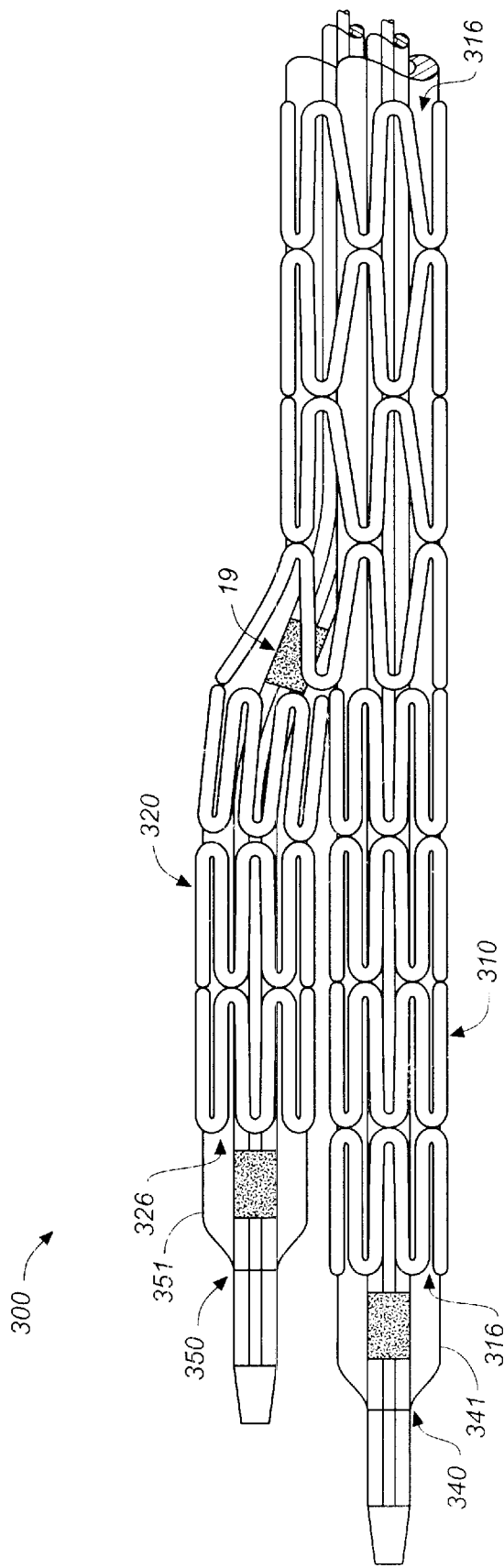
FIG._8B

ENDOLUMENAL PROSTHESIS AND METHOD OF USE IN BIFURCATION REGIONS OF BODY LUMENS

FIELD OF THE INVENTION

The present invention is a surgical device. More particularly, it is an endolumenal prosthesis which is adapted for use in bifurcated regions of body lumens. Still more particularly, it is an endovascular stent which is adapted to provide radial support to a main lumen of an endolumenal bifurcation and which includes a dilator and access device which are preloaded within a preselected side port along the endolumenal prosthesis prior to delivery of the endolumenal prosthesis to the bifurcation region in order to facilitate delivery of a second endolumenal prosthesis through the side port and into a side branch extending from the main lumen at the bifurcation region.

BACKGROUND

Conventional Stents

A wide range of medical treatments have been previously developed using "endolumenal prostheses," which terms are herein intended to mean medical devices which are adapted for temporary or permanent implantation within a body lumen. Examples of lumens in which endolumenal prostheses may be implanted include, without limitation: arteries, such as for example those located within the coronary, mesentery, peripheral, or cerebral vasculature; veins; gastrointestinal tract; and fallopian tubes. Various different types of endolumenal prosthesis have also been developed, each providing a uniquely beneficial structure to modify the mechanics of the targeted lumenal wall. For example, various grafts, stents, and combination stent-graft prostheses have been previously disclosed for implantation within body lumen. More specifically regarding stents or stent-grafts, various designs of these prostheses have been previously disclosed for providing artificial radial support to the wall tissue which forms the various lumens within the body, and usually more specifically within the blood vessels of the body.

One more frequently disclosed "stenting" treatment beneficially provides radial support to coronary, peripheral, mesentery or cerebral arteries in order to prevent abrupt reclosure subsequent to recanalization of stenosed vessels, such as by balloon angioplasty or atherectomy (mechanical dilation of stenosed vessel by radial balloon expansion or direct removal of stenotic plaque, respectively). In general, the angioplasty or atherectomy-type recanalization methods reestablish flow to reperfuse tissues downstream of an initial stenosis. Subsequent to such recanalization, however, the dilated lumen of the stenosis site may reocclude, such as by abrupt reclosure (usually due to acute thrombosis or dissected vessel wall flaps transecting the vessel lumen), restenosis (generally considered as a longer term "scarring"-type response to wall injury during recanalization procedures), or spasm (generally considered a response to overdilatation of a vessel and in some aspects may be a form of abrupt reclosure). The implantation of stents to mechanically support the vessel walls at such stenosis sites, either during balloon angioplasty or subsequent to recanalization, is believed to deter the reocclusion of such recanalized vessels which may otherwise occur due to one or more of these phenomena. Various categories of stents have therefore arisen for the primary purpose of providing endolumenal radial support primarily within arteries adjunctively to recanalization.

One criteria by which various stent designs may be generally categorized draws from the structural design which forms a particular stent's tubular wall. Various "tubular wall" types of stents according to this criteria include, without limitation: wire mesh stents; coiled stents; tubular slotted stents; and integrated ring stents. In general, each of these "tubular wall" categories of stents includes a network of integrated support members which combine to form a tubular stent wall that defines a longitudinal passageway. The structural integrity of the integrated support members provides radial rigidity against physiological collapse forces at the vessel wall, whereas the longitudinal passageway through the prosthesis allows for perfused flow through the stented region.

Another criteria by which various stent "types" may be categorized relates to the delivery method by which a particular stent is adapted for implantation within a lumen or vessel. In general, stents are delivered in a radially collapsed condition to the stenting site via known percutaneous translumenal procedures. Once positioned at the stenting site, the stent is adjusted to a radially expanded condition which is adapted to radially engage the interior surface of the wall tissue which defines the lumen, such as a vessel wall in an arterial stenting procedure. According to this generally applicable delivery mode, various stent categories which may be stratified by more particular delivery methods include, without limitation: "self expanding" stents, which generally expand under their own force once delivered to the desired stenting site; and "balloon expandable" stents, which generally expand under mechanical strain from an inflating balloon at the stenting site.

One specific example, within the previously disclosed "self-expanding" stenst is adjustable from the radially collapsed condition to the radially expanded condition by removing a radial constraining member once delivered to the stenting site. This type of self-expanding stent is adapted to recover from an elastically deformed state, when radially confined by the constraining member in the radially collapsed condition, to a resting or recovered state in the radially expanded condition, when radially unconstrained. Further detailed examples of known constraining members for use in delivery systems for such known "self-expanding" stents include either radially confining sheaths or releasable tethers which are releasably coupled to the stent wall when in the radially collapsed condition. Another more specific example of a previously disclosed "self-expanding" stent is adjustable from the radially collapsed condition to the radially expanded condition by heating the stent once delivered to the stenting site, thereby inducing a heat-memory recovery of the stent to the radially expanded condition.

Further to the previously disclosed "balloon expandable" stent variations, known stents according to this type are generally crimped or otherwise held in the radially collapsed condition over an exterior surface of an expandable balloon and are adjusted to the radially expanded condition by inflating the balloon. Further detail of previously known "balloon expandable" stent designs includes those which are provided "pre-loaded" onto a balloon catheter, and also those which may be provided separately to a physician user who may crimp the stent onto a balloon immediately prior to delivery in vivo.

Further more specific examples of stents according to the various "tubular wall" and "delivery method" categories just summarized above are disclosed variously throughout the following references: U.S. Pat. No. 4,580,568 to Gianturco; U.S. Pat. No. 4,733,665 to Palmaz; U.S. Pat. No. 4,739,762 to Palmaz; U.S. Pat. No. 4,776,337 to Palmaz; U.S. Pat. No.

4,830,003 to Wolff et al.; U.S. Pat. No. 4,913,141 to Hillstead; U.S. Pat. No. 4,969,458 to Wiktor; U.S. Pat. No. 5,019,090 to Pinchuk; and in U.S. Pat. No. 5,292,331 to Boneau. The disclosures of these references are herein incorporated by their entirety by reference thereto.

Conventional Bifurcation Stenting Techniques

Stenoses within bifurcation regions of lumens, more particularly of arterial lumens, have long presented a particular challenge to conventional recanalization techniques, and more particularly to conventional stenting techniques. For example, adjunctively to implanting a stent within a main vessel, which includes a side-branch vessel arising from the main vessel wall along the implanted stent's length, additional stenting of the side-branch vessel may also be required in order to maintain patency of that vessel. The various clinical indications or concerns which are believed to give rise to the desirability of such bifurcation stenting include: mechanical closure of an acutely bifurcating side-branch due to angioplasty of the main vessel or implantation of the main vessel stent; additional stenotic disease in the side-branch vessel; and flow reduction and poor hemodynamics into the side-branch from the main vessel due to the occlusive presence of the main vessel stents structure in the entrance zone to the side branch. However, it is further believed that conventional stent designs present significant mechanical and procedural challenges to successful stenting of both the main and side-branch vessels at bifurcations of body lumens, and particularly within arterial bifurcations.

One conventional bifurcation stenting technique which has been previously disclosed includes first stenting the side-branch and then the main vessel. However, several challenges and incumbent risks related to this alternative method have been disclosed. For example, angle variations or limited angiographic visualization at the side-branch take-off may prevent accurate placement of the first stent exactly in the ostium of the side-branch, thereby resulting in a sub-optimal result in the ostium. Furthermore, placement of the first stent too far proximally at the take-off may occlude and prevent subsequent stenting of the main vessel.

Another conventional bifurcation stenting technique which has been previously disclosed includes first stenting the main vessel and then advancing a second stent through the wall of the main vessel stent and into the side-branch where it is deployed. However, this technique is also generally believed to be challenging due to the main vessel stent's tubular wall which occludes or "jails" the side-branch from access with the side-branch stent.

According to the challenges of conventional bifurcation stenting techniques just summarized, several modified stent deployment procedures have therefore been developed in attempt to safely and accurately implant conventional stents into both the main vessel and also the side-branch vessel at bifurcation regions of body lumens. In addition, particular stent designs have also been disclosed which are specifically intended for implantation within a bifurcation region and which are alleged to enhance the delivery of a second side branch stent using otherwise conventional techniques.

Modern Bifurcation Stenting Techniques using Conventional Stents

Several modern bifurcation stenting techniques which modify the use of conventional stents in bifurcation stenting procedures have been disclosed by David P. Foley et al. in "Bifurcation Lesion Stenting," The Thoraxcentre Journal, Volume 8, Number 4 (December 1996), and include the "Monoclonal Antibody" approach; the "Culotte technique"; and the "Inverted Y" technique. The disclosure of this reference is herein incorporated in its entirety by reference thereto.

According to the "monoclonal antibody" approach disclosed in Foley et al., two guidewires are each delivered through an 8 French guiding catheter and into each of two branches at a bifurcation region, respectively, preferably using a 0.010" guidewire in the side-branch at the bifurcation. Either the bifurcation lesion is dilated in each of the branch vessels separately, or in a "kissing" balloon technique wherein two balloons are simultaneously inflated in the branch vessels, usually with some balloon overlap in the proximal main vessel. Then, a stent of appropriate length is deployed into the main vessel, thereby "jailing" the 0.010" wire in the side-branch vessel. Using the jailed 0.010" wire as a radiopaque landmark, an additional wire, also preferably 0.010" diameter, is then placed into the side branch through a gap between the support member of the main vessel stent's wall, after which the first "jailed" 0.010" guidewire is removed. A dilatation balloon is then advanced over the second 0.010" wire through the gap between the main vessel stent's support members, wherein the balloon is then inflated to dilate open the gap. A side-branch stent is then advanced through the dilated open gap and is deployed into the side-branch.

The "Culotte" technique disclosed in Foley et al. generally includes the following method. The first of two specific "Freedom" stents is implanted within the main vessel, including a first branch lumen of a bifurcation. A wire is then advanced through the side of the first stent and into the distal branch of the main vessel. The distal end portion of a second "Freedom" stent is then advanced over the wire and through the side of the first stent and into the second side branch lumen of the bifurcation, leaving the proximal end portio of the second "Freedom" stent within the proximal main vessel. According to this positioning, the second stent is implanted within both the second branch lumen and also in overlapping arrangement with the first stent in the main vessel. However, a risk of dissecting the side-branch is present in this technique because the side branch stent is oversized to that branch in order to properly engage the proximal main vessel.

According to the "Inverted Y" technique disclosed in Foley et al. and previously described by Antonio Colombo, two stents are each placed within first and second side branch lumens at a bifurcation region extending distally from proximal, main vessel lumen. Two guidewires are left in place within and through the implanted side branch stents. A third stent is then crimped onto two adjacent balloons which are adapted to track the indwelling guidewires to the proximal, main vessel lumen of the bifurcation region wherein the third stent is then implanted by expanding the two balloons adjacent to the first and second side branch stents. Further to the "Inverted Y" techniques just described, accurate positioning of each of three stents relative to the other stents is required, which may further require intracoronary ultrasound, and wire crossing particularly between delivery of the first two stents and the third stent may be a significant obstacle which may require a "test run" with the two balloon catheters prior to crimping the third stent thereover. Therefore, Foley et al. further discloses a modified variation of the "Inverted Y" technique, wherein the three stents described are together pre-loaded onto two long balloons such that the entire "bifurcation stent" may be placed in one manoeuvre. However, this modified vartiation is believed to by more bulky and rigid than the initial "Inverted Y" technique and may require very good predilatation and ideally a fairly proximally located and easy to reach bifurcation in reasonably large vessels.

Further disclosure of conventional stenting techniques is also provided by Freed, M. D., et al. in "The New Manual of Interventional Cardiology," Chapter 10, pp 238–243, Physicians' Press, 1996. The disclosure of this reference is herein incorporated in its entirety by reference thereto.

Modern "Bifurcation Stents"

Particular stent designs have also been disclosed which are specifically intended for use within arterial bifurcation regions. More particularly, two stent designs which appear to be specifically designed for use within arterial bifurcation regions, respectively called the "SITOstentRS" and the "JOStentRB", have been previously disclosed by "PENTACHI-SITOmed SrL" corporation located in Milan, Italy. In general, each of these particular stents includes a region along the stent tubular wall which has larger spaces or "side ports" between support members than are provided at other regions along the stent tubular wall.

More particularly regarding the previously disclosed "SITOStentRS," the widely spaced side port region appears to be positioned along a midportion of the stent tubular body, wherein it is bordered on either side by a more tightly structured tubular wall. The "SITOStentRS" further appears to be adapted for positioning along a main artery such that the widely spaced side port region along its midportion is aligned with a side branch extending from the main artery.

In contrast, the previously disclosed "JOStentRB" appears to provide the widely spaced side port region along one end portion, which appears to be the intended proximal end portion, of the stent tubular wall. The "JOStentRB" further appears to be adapted for positioning within a bifurcation region such that a distal, tightly integrated support member portion is located within a first branch lumen extending from the bifurcation zone, and such that the proximal, widely spaced side port region extends across the entrance zone to a second branch lumen extending from the bifurcation region and is further positioned only partially within the more proximal main or common artery. It further appears from the prior disclosure of the "JOStentRB" that the alignment of the relatively widely spaced side port region with the entrance zone of the second side branch artery is adapted to facilitate delivery of a second stent, which may be a second "JOStentRB", through one of those widely spaced side ports and into the second branch lumen for implantation adjacent to the bifurcation.

None of the cited references discloses an endolumenal prosthesis assembly with a tubular prosthesis body which is adapted for implantation within a bifurcation region of a body lumen such that a second prosthesis may be subsequently implanted within a side branch lumen extending from the bifurcation region along the length of the implanted tubular prosthesis body without the need to sub-select a side port along the tubular prosthesis body which is aligned with the side-branch and then deliver the second prosthesis through the sub-selected side port.

Nor do the cited references disclose an endolumenal prosthesis assembly with a tubular prosthesis body which is adapted for implantation within a main lumen of a bifurcation region of a body lumen, and wherein the prosthesis assembly is further adapted for preselecting a side port along the prosthesis body, prior to delivering the prosthesis body to a bifurcation region of a body lumen, which may then be aligned with one side branch lumen extending from the main lumen and through which a second prosthesis may be delivered and implanted within the side branch lumen.

Nor do the cited references disclose an endolumenal prosthesis assembly with a tubular prosthesis body which is adapted for implantation within a main lumen of a bifurcation region of a body lumen, wherein the prosthesis assembly further includes a dilator pre-engaged within and through a side port along the prosthesis body prior to implanting the prosthesis body within the main lumen, and which is further adapted such that the side port and dilator may be aligned with a side branch lumen extending from the main lumen subsequent to positioning the prosthesis body within the main lumen but prior to implanting the prosthesis body within the main lumen.

Nor do the cited references disclose an endolumenal prosthesis assembly with a tubular prosthesis body which is adapted for implantation within a main lumen of a bifurcation region of a body lumen, wherein the prosthesis assembly further includes an access device which is pre-engaged within and through a side port along the prosthesis body prior to implanting the prosthesis body within the main lumen, and wherein the prosthesis assembly is further adapted such that the side port and access device maybe aligned with a side branch lumen extending from the main lumen along the length of the prosthesis body subsequent to positioning the prosthesis body within the main lumen but prior to implanting the prosthesis body within the main lumen.

SUMMARY OF THE INVENTION

The present invention is an endolumenal prosthesis assembly which is adapted for engaging an interior surface of a body lumen wall at a bifurcation region of a body lumen, preferably within a main lumen of a bifurcation region in an arterial vascular tree. The assembly includes an expandable prosthesis therethrough which has an elongate prosthesis body with a proximal end portion, a distal end portion, a prosthesis passageway extending along the longitudinal length of the body, and a side port which is positioned along the body's length and through which the prosthesis passageway communicates externally of the elongate prosthesis body. The expandable prosthesis is adjustable from a radially collapsed condition, wherein the elongate prosthesis body has a collapsed outer diameter, to a radially expanded condition, wherein the elongate prosthesis body has an expanded outer diameter which is larger than the collapsed outer diameter. The distal end portion of a delivery member is coupled to the expandable prosthesis in order to deliver the expandable prosthesis to the bifurcation region in a percutaneous translumenal procedure. The distal end portion of an expansion member is also removably engaged with the elongate prosthesis body and is adapted to adjust the expandable prosthesis from the radially collapsed condition to the radially expanded condition.

In one mode of the invention, the distal end portion of a dilator is engaged within the prosthesis passageway and also within the side port and is adjustable from a first dilator position, wherein the side port has an initial inner diameter, to a second dilator position, wherein the side port is dilated to an expanded inner diameter which is larger than the initial inner diameter.

In one aspect of this mode, the dilator's distal end portion includes an expandable member which is engaged within the side port. The expandable member is adjustable from a radially collapsed condition, which characterizes the first dilator position, to an radially expanded condition, which characterizes the second dilator position. In a further variation of this aspect, the expandable member is an expandable balloon and is fluidly coupled to a dilator inflation lumen which is adapted to couple to a pressurizeable fluid source.

In another aspect of this mode, the dilator's distal end portion includes a taper with a distally reducing outer diameter from a large outer diameter portion to a small outer diameter portion. In the first dilator position, the small outer diameter portion is engaged within the side port, and in the second dilator position the large outer diameter portion is engaged within the side port.

In yet another aspect of this mode, the expandable prosthesis is an endolumenal stent which is adapted to provide radial support to the body lumen wall when the expandable prosthesis is expanded from the radially collapsed condition to the radially expanded condition. The side port of the endolumenal stent aspect of the invention is formed by a gap between adjacent support members which form the stent's tubular body. Further to this aspect, the stent may be self-expanding, in which case the expansion member is a radially confining sheath which is adjustable over the stent between a constraining position to a releasing position, or may be balloon expandable, in which case the expansion member is an expandable balloon.

In still a further aspect of this mode, a lateral expandable prosthesis is coupled at its proximal end portion to the elongate prosthesis body at a location adjacent to the side port. The lateral expandable prosthesis has a lateral elongate prosthesis body with a proximal end portion, a distal end portion, and a lateral prosthesis lumen extending between a proximal end port located along the proximal end portion of the lateral elongate prosthesis body and a distal end port located along the distal end portion of the lateral elongate prosthesis body. The lateral expandable prosthesis is also adjustable from a second radially collapsed condition, wherein the lateral elongate prosthesis body has a second collapsed outer diameter, to a second radially expanded condition, wherein the lateral elongate prosthesis body has a second expanded outer diameter. Further to this aspect, the dilator's distal end portion is also engaged within the lateral prosthesis lumen such that when the dilator is adjusted from the first dilator position to the second dilator position the lateral expandable prosthesis is expanded from the second radially collapsed condition to the second radially expanded condition.

In another mode of the invention, the assembly includes an access device with a proximal end portion and a distal end portion. The distal end portion of the access device is engaged within the prosthesis passageway and also within the side port when the expandable prosthesis is in both the radially collapsed and radially expanded conditions. According to this mode, the expandable prosthesis may be positioned at the bifurcation region with the distal end portion of the expandable prosthesis located within the first branch lumen and with the side port aligned with the entrance zone to the second branch lumen such that the access device is adapted to provide percutaneous translumenal access to the second branch lumen.

In one aspect of this mode, the access device includes a guidewire which has a proximal end portion and a distal end portion. The guidewire's distal end portion has a shaped, radiopaque tip region which is steerable by torquing the proximal end portion of the guidewire, and which is engaged within the prosthesis passageway and extends distally through the side port when the expandable prosthesis is in both the radially collapsed and the radially expanded conditions.

In another aspect of this mode, the access device includes a guidewire tracking member with a proximal end portion, a distal end portion which is engaged within the prosthesis passageway when the expandable prosthesis is in both the radially collapsed and the radially expanded conditions, and a guidewire lumen which is formed at least in part by the distal end portion of the guidewire tracking member. The guidewire lumen communicates externally of the guidewire tracking member through a distal guidewire port located along the distal end portion of the guidewire tracking member at or adjacent to the side port and also through a proximal guidewire port located along the guidewire tracking member proximally of the prosthesis passageway. The guidewire tracking member is adapted to track over a guidewire slideably received within the guidewire lumen through the proximal and distal guidewire ports, or alternatively to provide guidewire access to the second branch lumen at the bifurcation region through the guidewire lumen. Further to this aspect, the access device may also include both the guidewire tracking member and also a guidewire.

In another aspect of this mode, the expandable prosthesis is an endolumenal stent which is adapted to provide radial support to the body lumen wall when the expandable prosthesis is expanded from the radially collapsed condition to the radially expanded condition. The side port of the endolumenal stent aspect of this mode is formed by a gap between adjacent support members which form the stent's tubular body. Further to this aspect, the stent may be self-expanding, in which case the expansion member is a radially confining sheath which is adjustable over the stent between a constraining position to a releasing position, or may be balloon expandable, in which case the expansion member is an expandable balloon.

The present invention also includes a method of engaging an expandable prosthesis within an interior surface of a body lumen wall at a bifurcation region of a body lumen. The expandable prosthesis used according to this method has a longitudinal axis, a length along the longitudinal axis, a prosthesis passageway which extends along the longitudinal axis, and a side port located along the length and through which the prosthesis passageway communicates externally of the expandable prosthesis.

One mode of this method according to the present invention includes engaging a distal end portion of a dilator within the prosthesis passageway and also within the side port of the expandable prosthesis while the expandable prosthesis is in a radially collapsed condition.

One aspect of this mode further includes positioning the expandable prosthesis within the bifurcation region such that the proximal end portion of the expandable prosthesis is located within the common branch lumen, the distal end portion of the expandable prosthesis is located within the first branch lumen, and the side port is aligned with the entrance zone to the second branch lumen.

A further aspect of this mode also includes: after positioning the expandable prosthesis within the bifurcation region, dilating the side port with the distal end portion of the dilator from the initial inner diameter to an expanded inner diameter which is larger than the initial inner diameter. One additional variation of this further aspect includes engaging a distal end portion of a guidewire within the prosthesis passageway, through the side port, and within at least the entrance zone of the second branch lumen before dilating the side port with the dilator. Still other variations of this further aspect include: dilating the side port before adjusting the expandable prosthesis from the radially collapsed condition to the radially expanded condition within the bifurcation; dilating the side port while adjusting the expandable prosthesis from the radially collapsed condition to the radially expanded condition; and dilating the side port after adjusting the expanded prosthesis from the radially collapsed condition to the radially expanded condition.

Another mode of the method according to the present invention includes positioning a distal end portion of an access device within the prosthesis passageway and also within the side port while the expandable prosthesis is in a radially collapsed condition. In one variation of the access device a guidewire is provided, in another variation a guidewire tracking member is provided, and in still another variation both a guidewire and a guidewire tracking member are provided.

One aspect of this mode further includes: after engaging the distal end portion of the access device within the prosthesis passageway and side port of the expandable prosthesis, positioning the expandable prosthesis within the bifurcation region while in the radially collapsed condition such that the proximal end portion of the expandable prosthesis is located within the common branch lumen, the distal end portion of the expandable prosthesis is located within the first branch lumen, and the side port is aligned with the entrance zone to the second branch lumen. Still a further aspect includes: after positioning the expandable prosthesis within the bifurcation region, adjusting the expandable prosthesis with the expansion member from the radially collapsed condition to the radially expanded condition such that the distal end portion circumferentially engages the first branch lumen and the proximal end portion circumferentially engages the common branch lumen.

BRIEF DESCRIPTION OF THE DRAWINGS

FIG. 1 shows a perspective view of one endolumenal prosthesis assembly according to the present invention, wherein an expansion member on the distal end portion of a delivery catheter is shown engaged substantially within the prosthesis passageway formed by a prosthesis body of an endolumenal prosthesis which is further shown as a stent, and wherein an expandable member on the distal end portion of a dilator is shown engaged within a proximal portion of the prosthesis passageway and also through a side port along the prosthesis body of the endolumenal prosthesis.

FIG. 2 shows a perspective view of the endolumenal prosthesis assembly shown in FIG. 1, and shows the prosthesis assembly during one mode of use wherein the endolumenal prothesis is positioned within a main lumen of a bifurcation region of a body lumen and with the side port and distal tip of the dilator aligned with the entrance zone of a side branch lumen extending from the bifurcation region, and further shows the endolumenal prosthesis as it is expanded with the expansion member of the delivery catheter within the main lumen of the bifurcation region.

FIG. 3 shows a similar perspective view of the endolumenal prosthesis assembly as that shown in FIG. 2, and shows the prosthesis assembly during another sequential mode of use wherein the dilator is adjusted from a first dilator position to a second dilator position which is adapted to expand the inner diameter of the side port.

FIG. 4 shows a similar perspective view of the endolumenal prosthesis assembly as shown in FIGS. 2–3, and shows the prosthesis assembly during yet another mode of use wherein the expandable member of the dilator and expansion member of the delivery catheter is deflated to thereby leave the endolumenal prosthesis implanted within the bifurcation region such that the side port has a diameter which approximates the inner diameter of the entrance zone of the side branch lumen of the bifurcation region.

FIG. 5 shows a perspective view of a further endolumenal prosthesis assembly variation according to the present invention, wherein an expansion member on the distal end portion of a delivery catheter is shown engaged substantially within the prosthesis passageway formed by a prosthesis body of an endolumenal prosthesis which is further shown as a stent-graft, and wherein an expandable member on the distal end portion of a dilator is shown engaged within a proximal portion of the prosthesis passageway, through a side port along the prosthesis body of the endolumenal prosthesis, and also through an aperture formed by the graft member of the stent-graft prosthesis.

FIG. 6 shows a perspective view of a further endolumenal prosthesis assembly variation according to the present invention, wherein an expansion member on the distal end portion of a delivery catheter is shown engaged substantially within the prosthesis passageway formed by a prosthesis body of an endolumenal prosthesis which is further shown as a stent, and wherein an access device assembly is shown engaged within a proximal portion of the prosthesis passageway and extends externally of the prosthesis passageway through a side port along the prosthesis body of the endolumenal prosthesis.

FIG. 7 shows a perspective view of a further endolumenal prosthesis assembly variation according to the present invention, wherein an expansion member on the distal end portion of a delivery catheter is shown as a radially confining sheath which is coaxially engaged substantially around a prosthesis body of an endolumenal prosthesis which is further shown as a self-expandable stent, and wherein an access device assembly is shown engaged within a proximal portion of the prosthesis passageway and extends externally of the prosthesis passageway through a side port along the prosthesis body of the endolumenal prosthesis and also extends externally of the radially confining sheath through a longitudinal groove formed by that sheath.

FIG. 8A shows a perspective view of a further endolumenal prosthesis assembly variation according to the present invention, wherein a bifurcated stent is shown to include a first endolumenal prosthesis, which is shown as a stent, and is also shown to include a lateral prosthesis body which is engaged to the first endolumenal prosthesis such that a proximal lateral port of a lateral prosthesis passageway formed by the lateral prosthesis body is adjacent to and aligned with a side port formed along the prosthesis body of the first endolumenal prosthesis.

FIG. 8B shows a perspective view of the endolumenal prosthesis shown in FIG. 8A, although showing the prosthesis body which is a stent in a radially collapsed condition with an expansion member of a delivery catheter engaged within a prosthesis passageway extending through the prosthesis body and also with an expandable member of a dilator which is also an access device engaged within the prosthesis passageway, through a side port along the prosthesis body, and through the lateral prosthesis passageway.

DETAILED DESCRIPTION OF THE EMBODIMENTS

The present invention is a stent assembly and method adapted specifically for stenting bifurcation regions within body lumens, such as within the bifurcations within the coronary arterial tree. FIGS. 1–4 show various views and modes of use for one endolumenal prosthesis assembly variation of the present invention, wherein an endolumenal stent is adapted to be positioned within a bifurcation region with a dilator and access device engaged within a predetermined side port along the stent such that the side port may be aligned with a branch lumen extending from the bifurcation along the stent. FIG. 5 shows a further variation which substitutes a stent-graft for the stent previously shown in FIGS. 1–4 as the endolumenal prosthesis in the overall combination prosthesis assembly. FIG. 6 shows still another endolumenal prosthesis assembly according to the present invention wherein an access device assembly is substituted for the dilator provided in the embodiment of FIGS. 1–4 and is pre-loaded within the side port of an endolumenal prosthesis and is further adapted to align the side port with a side branch lumen of a bifurcation and also to facilitate delivery of a dilator through that side port subsequent to implanting the endolumenal prosthesis. FIG. 7 shows a self-expanding stent variation which uses a delivery sheath with a longitudinal groove as the expansion member which is adapted to implant the endolumenal prosthesis within a bifurcation. A further, highly beneficial bifurcated stent embodiment according to the present invention is also shown in FIGS. 8A–B.

By specific reference to FIG. 1, endolumenal stent prosthesis assembly (1) is shown to include an endolumenal prosthesis (10) which is coupled to a delivery catheter (20) and also to a dilator (30). More particularly, endolumenal prosthesis (10) is shown in FIG. 1 as one specific endovascular stent variation, and is similar in design and construction to that described in pending U.S. patent application Ser. No. 08/702,258 which is expressly incorporated by reference herein, and in U.S. Pat. No. 5,292,331 to Boneau, the disclosure of which has been previously incorporated by reference above. For the purpose of further illustration, however, the stent which comprises endolumenal prosthesis (10) includes a series of adjacent rings or circular wires which form support members, such as is shown for the purpose of illustration at support member (11). Each ring is crimped or otherwise formed to include a secondary, sinusoidal shape which includes a plurality of substantially straight struts connected at axial bends or peaks, such as is shown for example at strut (12) which extends between peaks (13,14), respectively. Each ring is further secured to an adjacent ring at least at one location where the peaks of their sinusoidal shape meet, resulting in an overall structure of integrated support members which form tubular body (15). Tubular body (15) further forms a prosthesis passageway (16) extending through the plurality of adjacent, sinusodially-shaped rings along longitudinal axis L and between proximal prosthesis port (17) and distal prosthesis port (18).

Further to the networked structure of support members which form tubular body (15) as shown in FIG. 1, spaces remain along tubular body (15) between adjacent peaks of each shaped ring and also between adjacent rings, particularly where the individual peaks of adjacent rings extend away from each other relative to longitudinal axis L. These spaces may be considered as side ports through which prosthesis passageway (16) communicates externally of tubular body (15), as is shown for example at side port (19). The terms "side port" are therefore herein intended to mean a region along the tubular wall or body which makes up the stent or prosthesis through which the prosthesis passageway extending through the prosthesis body communicates externally of the prosthesis body. Further examples of "side ports" according to this definition include, without limitation: a discretely defined region of space which is surrounded on all sides by a support member, which may be further illustrated by a space formed and discretely defined between adjacent support members of a braided wire mesh or slotted tube; or a selected portion of a larger region of space, such as for example a selected space between two specifically adjacent turns of a wound coil which further has a plurality of spaced turns that otherwise form a contiguous, helical space along the separation between coil turns.

The distal end portion of delivery catheter (20) is shown in FIG. 1 to include an expansion member (21) which is a balloon that is fluidly coupled to a coaxial lumen (23) formed between an outer member (24) and inner member (25). Coaxial lumen (23) terminates along the proximal end portion of delivery catheter (20) in a proximal port (not shown) which is adapted to couple with a pressurizable fluid source. Expansion member (21) is further shown in FIG. 1 positioned within prosthesis passageway (16) such that tip (22) extends distally through distal prosthesis port (18) of endolumenal prosthesis (10). In this arrangement, expansion member (21) is adapted to adjust endolumenal prosthesis (10) from a first radially collapsed condition to a radially expanded condition by expanding or inflating the balloon with fluid from a pressurizeable fluid source.

The distal end portion of delivery catheter (20) is further shown in FIG. 1 to include a guidewire lumen (26) which is formed at least in part by inner member (25) and which terminates distally in distal guidewire port (27) which is located distally of expansion member (21). Guidewire lumen (26) further terminates in a proximal guidewire port along the proximal end portion of delivery catheter (not shown), the proximal guidewire port either including or being adapted to couple with a hemostatic valve. In this arrangement, delivery catheter (20) provides a delivery member which is adapted to slideably receive and track over a guidewire (not shown in FIG. 1) into the desired bifurcation site for treatment in a remote percutaneous translumenal procedure, as is described in more detail below.

Prosthesis assembly (1) shown in FIG. 1 further includes a dilator (30) which may have a similar design and construction as previously shown and described by reference to delivery catheter (20) also in FIG. 1. However, the distal end portion of dilator (30) includes an expandable member (31) which is positioned within only a proximal region of prosthesis passageway (16) such that tip (32) of dilator (30), which includes distal guidewire port (37) of guidewire lumen (36), and also a portion of expandable member (31) extends externally of prosthesis passageway (16) through side port (19). According to this arrangement, dilator (30) is adjustable from a first dilator position, which is characterized by a radially collapsed condition for expandable member (31), to a second dilator position, which is characterized by a radially expanded condition for expandable member (31). By adjusting the dilator between positions in this manner, the dilator is adapted to expand the side port (19) from an initial inner diameter to an expanded inner diameter which is larger than the initial inner diameter.

Dilator (30) is further shown in FIG. 1 to include a radiopaque marker (33) (shown in shadow) which is provided on the distal end portion of dilator (30) where engaged within side port (19). In the particular variation shown, radiopaque marker (33) is provided on an inner member which forms a guidewire tracking member with guidewire lumen and which extends within expandable member (31). Radiopaque marker (33) may be constructed for example of a metallic band which is comprised of radiopaque material, such as a metal containing gold, platinum, or tungsten, wherein the band is engaged to an outer diameter of the inner member such as by necking the inner member, which may be formed of an irradiated polymeric tubing, coaxially disposing the radiopaque band over the necked inner member, and then recovering the inner member under elevated heat. In addition or in the alternative, such a radiopaque band may also be simply adhered to the outer surface of the inner member such as by the use of adhesives. In any case, the inclusion of radiopaque marker (33) at side port (19) allows a physcian user, under X-Ray or fluoroscopic visualization, to track the assembly to the proper position within a target bifurcation region such that the side port is aligned with the side branch prior to implantation of the endolumenal prosthesis in the main lumen.

Further to this beneficial feature for positioning side port (19) by means of radiopaque marker (33) according to the FIG. 1 embodiment, the present invention further contemplates providing a similar "side port" marker along the other dilator or access devices where they are engaged within the side port of an endolumenal prosthesis according to the other embodiments which are otherwise herein shown or described by reference to the various Figures of this disclosure. Moreover, the present invention further contemplates providing a radiopaque marker on the endolumenal prosthesis body, such as on a stent, at a location which is at or adjacent to a side port according to the present invention.

Alternative designs may also be substituted for the specific design for dilator (30) shown in FIG. 1 without departing from the scope of the present invention. In one specific alternative dilator example not shown, an elongate member may include a taper on its distal end portion with a distally reducing outer diameter from a large outer diameter portion to a small outer diameter portion. The first dilator position for this variation is therefore characterized by engaging the small outer diameter portion within the side port, whereas the second dilator position is characterized by engaging the large outer diameter portion within the side port.

FIG. 2 further shows prosthesis assembly (1) during one mode of use, wherein endolumenal prosthesis (10) is positioned within a main lumen (110) of a bifurcation region (105) of a body lumen (100), which may be for example a bifurcation region of the coronary arterial tree. First and second guidewires (40,50) are shown respectively positioned within the distal branch (112) of main lumen (110), which may be herein considered the "first side branch" of the bifurcation region, and within side branch (114), which is also therefore considered the "second side branch" of the bifurcation.

Therefore, by further reference to the lumenal "bifurcation region" shown and described by reference to all the Figures which herein illustrate intended modes of using the present invention, various terms are herein used interchangeably to describe the various lumenal structures forming such bifurcations. For example, reference to a bifurcation region formed by a "main lumen" with a "side branch" extending therefrom may be interchangeably described by reference to a "main lumen" or "proximal, common lumen" which has a "first branch" lumen and "second branch" lumen extending therefrom to form the bifurcation. Moreover, the lumen in which the proximal portion of the endolumenal prosthesis of the various embodiments is implanted is generally interchangeably referred to as the "proximal branch of the main lumen", or "proximal, common lumen". Furthermore, the lumen in which the distal portion of the endolumenal prosthesis is implanted is herein interchangeably described as the "distal branch of the main lumen" or "first side branch lumen" or "first branch lumen". Still further, the lumen with which the side port of the endolumenal prostheses of the various embodiments is to be aligned in order to deliver or implant a side branch stent therethrough is herein described generally as the "side branch lumen", or may be interchangeably described where appropriate as the "second side branch lumen" or "second branch lumen". Thus, the intended use of the present invention contemplates both a truly bifurcating main lumen into two similar, distal side branches as well as bifurcations which are formed by a side branch arising from a main lumen.

Further to the positioning mode of use shown illustratively in FIG. 2, guidewires (40,50) are further slideably received within and through the respective guidewire lumens (26,36) of delivery catheter (20) and dilator (30), respectively. By positioning the guidewires in the branched lumens and engaging them with the dilator and delivery catheter as shown and just described, endolumenal prosthesis (10) is advanced into the bifurcation region and positioned there as shown in FIG. 2 by means of advancing delivery catheter (20) over guidewire (40) and dilator (30) over guidewire (50).

Either or both of delivery catheter (20) and dilator (30) may engage the respective guidewire in an "over-the-wire" design, wherein the respective guidewire lumen runs the full length of the device from a proximal guidewire port (not shown) positioned externally of the body to the respective distal guidewire port shown in FIG. 2. Or, each or both of delivery catheter (20) and dilator (30) may instead be a "rapid exchange" or "monorail" type design wherein only the distal end portion of the device tracks over the respective guidewire as a rail to the intended position shown. In addition, the present invention further contemplates a variation wherein delivery catheter (20) is alternatively provided in a previously known "fixed wire" design such that a guidewire is engaged with the delivery catheter in a torquable although relatively fixed configuration.

Endolumenal prosthesis (10) is further shown in FIG. 2 after being adjusted with the balloon of expansion member (21) from the radially collapsed position during delivery to the bifurcation and to a radially expanded condition. In the radially expanded condition shown, endolumenal prosthesis (10) has an outer diameter which is adapted to radially engage the interior wall of the main vessel lumen at the bifurcation region. Particularly regarding the highly beneficial embodiment shown which is adapted for use in coronary arterial bifurcations, this expanded outer diameter for expansion member (21) is preferably within the range of 1.0 to 5.0 mm in order to radially engage most coronary arterial vessels which fall within that range.

FIG. 3 shows prosthesis assembly (1) in a sequential mode of use subsequent to that shown in FIG. 2, wherein expandable member (31) of dilator (30) is shown expanded from a radially collapsed condition to a radially expanded condition. Expandable member (31) in the radially expanded condition is further shown partially within side port (19) of endolumenal prosthesis (10) and also extending partially distal from side port (19) and into side branch (114). According to this arrangement, expandable member (31) in the radially expanded condition has an outer diameter which is adapted to radially engage the lumenal wall which forms side branch (114). Furthermore, the outer diameter of expandable member (31) in the radially expanded condition shown is also adapted to adjust side port (19) from an initial inner diameter to a larger expanded inner diameter which approximates the inner diameter of the entrance zone of side branch (114) from main lumen (110). As previously described above by reference to expansion member (21) for the delivery catheter (20), in the highly beneficial coronary arterial application of the present invention the outer diameter of expandable member (31) in the radially expanded condition is within the range of 1.0 to 5.0 mm. However, it may be further preferred to provide expandable member (31)

at a slightly reduced outer diameter to that provided by the expansion member of the delivery catheter in order to suitably accommodate the generally reduced diameter of side branch vessels arising from a main lumen in a bifurcation.

Various balloon constructions and designs may be suitable for use as the delivery catheter's expansion member and also the dilator's expandable member as shown and described variously throughout the Figures according to the present invention. In one suitable variation, a relatively compliant balloon may be provided, such as for example a balloon comprised of polyolefin copolymer ("POC"), polyvinyl chloride ("PVC"), or low or linear low density polyethylene. Alternatively, a relatively non-compliant balloon may be provided, particularly in the case where high pressures are desired, such as for example a balloon comprised of polyester terepthalate ("PET"), polyimide, or high density polyethylene.

More specifically regarding the terms "initial inner diameter" and "expanded inner diameter" which are herein used to described the side port of the endolumenal prosthesis according to the present invention, these terms are herein intended to describe the spacing between support members which are engaged around the dilator and as viewed in cross section across the entrance zone to the side branch lumen from the main vessel. Therefore, whereas the actual space which forms the side port along the prosthesis body may present a highly complex geometry defined by a particular pattern of support members, the "inner diameter" herein used to describe the side port is an "effective" inner diameter which is limited by the smallest spacing between support members taken across the side branch entrance zone. Furthermore, at least one support member which in part defines the side port may be forced radially outwardly to extend from the prosthesis wall and into the entrance zone of the side branch lumen, as is shown for the purpose of further illustration at support member (19') in FIGS. 3 and 4.

FIG. 4 shows prosthesis assembly (1) in still a further sequential mode of use subsequent to that shown in FIG. 3, showing prosthesis assembly (1) after expansion of endolumenal prosthesis (10) to radially engage the interior wall of main lumen (110) and also after expansion of side port (19) to a radially expanded inner diameter which approximates the inner diameter of side branch (114). Expandable member (31) of dilator (30) is further shown in FIG. 4 after being deflated back to a radially collapsed condition and while being withdrawn from prosthesis passageway (16) over guidewire (50), whereas guidewire (50) is left remaining within prosthesis passageway (16), side port (19), and side branch (114).

According to the operational mode for prosthesis assembly (1) shown in FIG. 4, both dilator (30) and delivery catheter (20) may be removed from the body over their respectively engaged guidewires, and furthermore guidewire (40) may also be removed along with delivery catheter (20). Once endolumenal prosthesis (10) is deployed as just shown and described by reference to FIGS. 2–4, a second prosthesis may be delivered over guidewire (50), through prosthesis passageway (16) and expanded side port (19), and into side branch (114) where it may be implanted adjacent to side port (19) to complete the bifurcation stenting procedure.

Further to the sequential modes of use just illustrated by reference to FIGS. 2 and 3, the present invention contemplates various other modes for reaching the result of implanting an endolumenal prosthesis with an expanded side port within an intended bifurcation region as shown in FIG. 4. In one variation, the method of dilating the side port is performed before adjusting the expandable prosthesis from the radially collapsed condition to the radially expanded condition within the bifurcation region. In a further variation, the method of dilating the side port is performed while adjusting the expandable prosthesis from the radially collapsed condition to the radially expanded condition within the bifurcation region.

In addition to the various alternative methods just described for expanding the endolumenal prosthesis and also the side port, a further variation not shown is believed to be particularly beneficial in cases where the bifurcation region presents a risk for abrupt closure of the side branch vessel of an arterial bifurcation during expansion of the endolumenal prosthesis within the main lumen of the bifurcation (the bifurcation of which includes a proximal, common branch lumen and first and second branch lumens extending therefrom). According to this variation, the expandable balloon of the dilator is advanced distally beyond the side port and into the second branch lumen before adjusting the expandable prosthesis to its respective radially expanded condition and also before adjusting the side port to the expanded inner diameter. Then, either before or while adjusting the expandable prosthesis to its respective radially expanded condition, the expandable balloon is pressurized with fluid from a pressurizeable fluid source such that the expandable balloon is adjusted from its respective radially collapsed condition to its respective radially expanded condition which circumferentially engages an interior wall of the second branch lumen. While the dilator's expandable balloon is radially engaged with the second branch lumen, the expandable prosthesis is then adjusted to its respective radially expanded condition within the first branch lumen and the common branch lumen.

According to this method just described, it is believed that by inflating the side branch balloon during or prior to inflating the main lumen balloon, plaque which may be located at the bifurcation is prevented from otherwise being pushed from the main branch and into the side branch. Subsequently, after adjusting the endolumenal prosthesis to its respective radially expanded condition within the first branch lumen and the common branch lumen, the expandable balloon of the dilator is then deflated and withdrawn proximally until it is positioned at least partially within the side port for subsequent expansion of the side port.

It is believed that the operational modes just described sequentially by reference to FIGS. 2–4, in addition to the other variations described but not shown, are particularly beneficial in bifurcation stenting procedures wherein both the first endolumenal prosthesis and also the second endolumenal prosthesis delivered through the side port comprise stents. Moreover, again according to the operational modes of using the assembly of the present invention as just described, this side branch stenting may be accomplished without the need to sub-select the side branch with a guidewire through the spaces between support members of the expanded stent in the main vessel. This is because the pre-engaged dilator within the preselected side port along the prosthesis body, together with the respectively engaged guidewire, provides an access device through the side port which is adapted to position the side port adjacent to the side branch where it may then be dilated. To that end, the present invention according to the operational modes shown and described further eliminates the need to advance a second balloon catheter through the side port formed between adjacent support members or stent "struts" prior to dilating that port.

Other specific stent designs than that just previously shown and described by reference to endolumenal prosthesis (10) in FIGS. 1–4 may also be amenable to the combination assembly of the present invention according to one of ordinary skill based upon this disclosure. For example, one or more alternative stent designs, such as those disclosed and previously incorporated by reference above, may also provide a side port and be suitably adapted to couple with a dilator or access device according to overall assembly of the present invention as herein described. More specifically, various known or modified coiled wire and slotted tube designs may be substituted for the stent shown and described for endolumenal prosthesis (10) in FIG. 1 without departing from the scope of the present invention. In addition, other endolumenal prosthesis variations may also be suitable for use in an assembly with a dilator or access device as described by reference to the embodiments shown in FIGS. 1–4, including for example grafts, stent-grafts, and self-expanding stents or stent-grafts.

FIG. 5 shows another prosthesis assembly (150) according to the present invention which includes one further endolumenal prosthesis variation to that shown and described by reference to FIGS. 1–4. More specifically, endolumenal prosthesis (160) is shown in FIG. 5 as a stent-graft design and includes a stent (165), which is shown for the purpose of illustration to be a similar design to endolumenal prosthesis (10) in FIGS. 1–4, and a graft member (170) coupled to stent (165). Graft member (170) further includes an aperture (172) which is aligned with side port (169) through which prosthesis passageway (166) formed by endolumenal prosthesis (160) communicates externally of endolumenal prosthesis (160). Prosthesis assembly (150) further includes a delivery catheter (180) which is similar to delivery catheter (20) shown in FIGS. 1–4 and which extends through prosthesis passageway (166), and also includes a dilator (190) which is similar to dilator (30) shown in FIGS. 1–4 and which is coupled within a proximal portion of prosthesis passageway (166) and extends through side port (169).

Graft member (170) is shown in FIG. 5 to coaxially surround an outer surface of the prosthesis body which forms stent (165). However, the present invention further contemplates other designs for the stent-graft variation of FIG. 5, such as for example providing a graft member engaged to an internal surface of the prosthesis body which forms the stent member of the composite assembly, or in a further example providing a graft member on both the outer and inner surfaces of the stent component. Notwithstanding these variations, other known stent-graft designs may be modified to include an aperture and side port through the graft and stent members, respectively, and be suitably used according to the combination assembly provided by the embodiment shown in FIG. 5.

In addition to the expansion members provided by the dilators shown and described by reference to the previous embodiments throughout FIGS. 1–5, those dilators additionally provide an access device assembly, via a guidewire lumen and guidewire which is coaxially engaged within that lumen, which is pre-loaded within the relative prosthesis passageway, side port, and aligned side branch prior to implanting the endolumenal prosthesis within a main lumen at a bifurcation. As previously described, this guidewire tracking functionality for the dilator allows the side port and dilator to be positioned adjacent to and aligned with the side branch such that the subsequently dilated side port provides a window into that side branch for delivering a side branch stent. However, it is further contemplated that providing such a side branch access device pre-loaded through the main lumen prosthesis is beneficial independently of providing an actual dilator preloaded into the prosthesis assembly before implantation.

FIG. 6 shows one particular access device assembly variation according to the present invention which does not provide a dilator and which is pre-loaded within the endolumenal prosthesis in order to provide percutaneous translumenal access to a side branch through a side port in the endolumenal prosthesis. Prosthesis assembly (200) is shown in FIG. 6 to include an endolumenal prosthesis (210) which may be similar in design and construction to the endolumenal prosthesis (10) previously shown and described by reference to FIGS. 1–4. In addition, prosthesis assembly (200) also includes a delivery catheter (220) which also may be similar in design and construction to delivery catheter (20) as previously shown and described by reference to FIGS. 1–4. However, rather than providing a dilator with an expandable member which is pre-loaded and engaged within the prosthesis passageway and side port of the endolumenal prosthesis, the FIG. 6 embodiment instead provides a simple access device assembly (230) in a preloaded arrangement.

More specifically, access device assembly (230) is shown in FIG. 6 to include a tubular member (232) which includes an access lumen (234) that terminates distally at distal access port (236) located at the distal tip of tubular member (232). Access lumen (234) also extends proximally along tubular member (232) and terminates proximally in a proximal access port located at the proximal end portion of tubular member (232) (not shown) which is adapted for user access during in vivo use of prosthesis assembly (200). Moreover, the distal tip of tubular member (232) which includes distal access port (236) is shown in FIG. 6 extending through side port (219). Guidewires (240,250) are shown respectively engaged within guidewire lumen (226) of delivery catheter (220) and access lumen (234) of tubular member (232).

Prosthesis assembly (200) as shown in FIG. 6 may be beneficially used according to the following method (not shown). Guidewire (240) may be advanced and subselectively positioned within a distal branch of the main lumen of a targeted bifurcation region (not shown) and guidewire (250) may be similarly positioned within a side branch extending from that bifurcation region. By advancing prosthesis assembly (200) with delivery catheter (220) and access device (230) respectively tracking over these guidewires (240,250), the distal end portion of endolumenal prosthesis (210) may be positioned within the distal branch of the main lumen such that side port (219) and the distal tip of tubular member (232) are aligned with the entrance zone of the side branch prosthesis assembly (200) is further shown extending.

Alternatively to the method just described, further variations of placing the guidewires and tracking the various components of the prosthesis assembly thereover are also contemplated. In one highly beneficial variation, guidewire (240) is first positioned within the distal branch of the main lumen of the bifurcation. The overall prosthesis assembly is then tracked over guidewire (240) until side port (219) is aligned with the intended side branch for bifurcation stenting. Then, guidewire (250) is advanced into the side branch. The present invention further contemplates these various modes of operation regarding guidewire tracking arid positioning of the assembly will equally apply to the other embodiments herein shown or described.

In a subsequent operational mode according to this arrangement, endolumenal prosthesis (210) may be expanded and implanted within the main vessel by way of expansion member (221), after which delivery catheter (220) and tubular member (232) may be withdrawn over guidewires (240,250), respectively. Guidewire (240) is thereby left remaining engaged within prosthesis passageway (216), side port (219), and the side branch lumen which is aligned with side port (219). A dilator which may be a balloon catheter similar to dilator (10) of FIGS. 1–4 may then be advanced over guidewire (250) and through prosthesis passageway (216) until engaged within side port (219) where it may then be used to expand the bore formed by side port (219) such that an additional side branch stent may be delivered therethrough.

Other specific access device designs may also be suitably substituted for the specific access device assembly (230) shown for prosthesis assembly (200) in FIG. 6 without departing from the scope of the present invention. For example, a guidewire such as guidewire (250) shown in FIG. 6 may be suitably preloaded within the prosthesis passageway and side port of the endolumenal prosthesis without the inclusion of a tubular member engaged to the guidewire. Still further, such an embodiment may also provide a folded design for the balloon expansion member on the delivery catheter when in the radially collapsed condition such that the guidewire is slideably disposed within the balloon's folds proximally of the side port. However, while these alternative access device variations may be suitable without a tubular member, it is believed that the inclusion of the tubular member such as shown in the FIG. 6 variation provides a highly beneficial slideable engagement which enhances the ability to manipulate the distal tip of the guidewire for preselecting the target side branch and which also enhances the trackability of the prosthesis assembly over the guidewire to align the side port with the side branch.

Further to the various "access device assemblies" just described, the terms "access device assembly" or "access device" or variations thereof are herein intended to mean suitable medical device assembly which is adapted to provide remote in vivo access for a user to perform medical procedures within a preselected site within the body. The illustrative "access device assembly" embodiments previously provided therefore include: a guidewire which provides a rail over which other object devices may track to the preselected site; a tubular body which provides a lumen through which other object devices may be advanced to the preselected site, such as by further example a lumen which provides a guidewire tracking member that slideably engages a guidewire; and a combination assembly of a guidewire and tubular member with guidewire tracking member.

In still a further access device variation, a tubular member such as tubular member (232) shown in prosthesis assembly (200) in FIG. 6 may also be coupled to the delivery catheter which is adapted to deliver and implant the endolumenal prosthesis of the assembly within a main vessel of a bifurcation. Further to this variation, the tip region of the tubular member may extend through the side port as shown for tubular member (232) in FIG. 6 while the rest of the tubular member proximally thereof is coupled to the delivery catheter including the proximal region of the expansion member proximally of the prosthesis side port such as by bonding the tubular member to the expandable member. To that end, it is further contemplated according to the various embodiments described throughout this disclosure may additionally be modified to engage the dilator or access device with the delivery catheter to create one delivery unit that is adapted at its distal end to perform the various functions herein described.

In still another particular endolumenal prosthesis variation, a self-expanding, preferably shape memory stent or stent-graft may be substituted for the balloon expandable variation previously shown and described by reference to FIGS. 1–4, as is shown in FIG. 7 at endolumenal prosthesis assembly (270). In more detail, prosthesis assembly (270) includes a self-expanding stent (275) which is coupled to an expansion member (280) which is shown as a slideable delivery sheath which is adjustable from a first position, which coaxially confines the self-expanding stent (275) in a radially collapsed condition (shown in FIG. 7), to a second position, which releases the stent from confinement and allows self-expanding stent (275) to relax to the radially expanded condition (not shown). In the specific variation of FIG. 7, expansion member (280) is adjustable from the first position to the second position by withdrawing the sheath proximally over and from self-expanding stent (275).

Still further to FIG. 7, the distal end portion of expansion member (280) preferably includes a longitudinal groove (285) which is registered with the distal tip of a dilator (290) which is also an access device, as previously shown and described by reference to the previous embodiments, which extends through the side port (277) of the coaxially confined self-expanding stent (275). According to this arrangement, the side port (277) and tip of the dilator (290) may communicate through the groove (285) and be aligned with the side branch of a bifurcation when the distal region of the endolumenal prosthesis is positioned within the distal branch of the main lumen or vessel and also while the delivery sheath remains coaxially disposed over the radially confined prosthesis. The longitudinal groove (285) further facilitates proximal withdrawal of the distal end portion of the expansion member (280) in the region of side port (277).

FIG. 8A shows bifurcation stent (300) as a further endolumenal prosthesis variation for use in stenting bifurcation regions of body lumens according to the present invention. Bifurcation stent (300) as shown in FIG. 8A includes a first endolumenal prosthesis (310), which is adapted for delivery to and implantation within a main lumen of a bifurcation, and also includes a lateral prosthesis (320), which is engaged to the first endolumenal prosthesis (310) and which is adapted for delivery to and implantation within a side branch extending from the main lumen when endolumenal prosthesis (310) is positioned within that man lumen.

More particularly, endolumenal prosthesis (310) is shown in FIG. 8A as an endolumenal stent which includes a network of integrated support members (314) that form prosthesis body (315) which further defines a prosthesis passageway (316), and is therefore similar in design and construction to endolumenal prosthesis (10) shown and described previously by reference to FIGS. 1–4. Lateral prosthesis (320) additionally is shown to include a similar design and construction as that shown for endolumenal prosthesis (310) in FIG. 8A or endolumenal prosthesis (10) in FIGS. 1–4, and incldues a lateral prosthesis body (325) that forms a lateral prosthesis passageway (326) which extends between proximal and distal lateral ports (327,328), respectively. However, at least one region along lateral prosthesis body (325) adjacent to proximal lateral port (327) is engaged to endolumenal prosthesis (310) such that proximal lateral port (327) is aligned with side port (319).

Still further to the variation shown in FIG. 8A, an engagement is formed between one peak of a support member which forms the proximal end port (327) of lateral prosthesis passageway (326) for lateral prosthesis (320) and one peak of a support member which defines in part the space along prosthesis body (315) which forms side port (319) along endolumenal prosthesis (310), as is shown at interface (330) in FIG. 8A. This interface (330) between adjacent peaks is preferrably welded or soldered, although it may be engaged by other methods as would be apparent to one of ordinary skill. Nevertheless, lateral prosthesis passageway (326) is in communication with prosthesis passageway (316) by way of the alignment between proximal lateral port (327) and side port (319).

Each of endolumenal prosthesis (310) and lateral prosthesis (320) is shown in FIG. 8A in its respective, radially expanded condition. However, each of endolumenal prosthesis (310) and lateral prosthesis (320) is adjustable to its radially expanded condition from an initial, radially collapsed condition which has a smaller outer diameter which facilitates percutaneous translumenal delivery of bifurcated stent (300) to the bifircation, as is shown in FIG. 8B.

Preferably, the radial adjustment for both endolumenal prosthesis (310) and lateral prosthesis (320) is achieved by an expansion member which may take the form for example of an expandable balloon. Therefore, for the purpose of further illustration, an expandable balloon (341) of a delivery catheter (340), which may be similar to expansion member (21) shown on delivery catheter (20) in FIGS. 1–4, is shown in FIG. 8B engaged within and through prosthesis passageway (316). Another expandable balloon (351) on the distal end of a dilator (350), which may be similar to expandable member (31) shown on dilator (30) in FIGS. 1–4, is also shown in FIG. 8B engaged within a proximal region of prosthesis passageway (316), through side port (319), and within lateral prosthesis passageway (326). Both expansion member (340) and expandable member (350) are preloaded prior to remote percutaneous translumenal delivery to the intended bifurcation site, and are further provided with guidewire tracking means for delivering the bifurcated stent (300) as previously described by reference to the other embodiments.

Still further to FIG. 8B, lateral prosthesis (320) is adapted to lay adjacent to the distal end portion of endolumenal prosthesis (310) when both components are in their radially collapsed condition during remote in vivo delivery of bifurcated stent (300). It is further believed that the inclusion of lateral prosthesis (320) adjacent to endolumenal prosthesis (310) may increase the profile of the overall bifurcated stent assembly versus stents which are absent such a laterally engaged device, including the non-bifurcated prostheses previous described by reference to the embodiments shown in FIGS. 1–4. Therefore, it is contemplated according to this variation that sufficient delivery catheters such as guiding catheters and introducer sheaths may require a larger inner diameter than those which are adapted to deliver other non-bifurcated prosthesis into remote endolumenal bifurcation regions.

The various embodiments and variations thereof have been previously described by reference to general use in endolumenal bifurcations, although one particularly useful operational mode of the present invention is in the percutaneous translumenal treatment of bifurcation lesions in the coronary vascular tree. In general, the overall procedure for using the devices and methods of the present invention according to this coronary arterial bifurcation mode of use is as follows.

Percutaneous access to an artery, preferably a peripheral artery, and more particularly one of the femoral arteries, may be first gained by way of a well known "Seldinger" technique. According to this access method, the femoral artery is first punctured with a needle. An introducer wire is then advanced retrogradedly into the femoral artery through the needle, after which the needle is replaced by a tapered dilator which is used to dilate open the puncture wound. The dilator may then either be replaced with an introducer sheath or an introducer sheath may be advanced over the dilator, in either case the distal end portion of the introducer sheath is left indwelling retrogradedly into the femoral artery while the proximal end portion of the introducer sheath is provided with hemostatic valve adapted to maintain relative hemostasis through the bore of the introducer. A guiding catheter coaxially disposed over a shaped guidewire is then introduced through the introducer sheath and is advanced retrogradedly along the aorta and aortic arch where it is then seated within the desired coronary arterial ostium which leads to the desired bifurcation for treatment. The guidewire is then withdrawn, leaving the guiding catheter as a conduit for delivering the assemblies of the present invention to the branched vessels leading to the treatment site.

In the alternative to the "Seldinger" technique just described, other access procedures may alternatively be used for introducing the devices and assemblies of the present invention into the desired bifurcation region. For example, other known "cut-down" techniques, which involves directly cutting open a region of an artery as an "arteriotomy" and inserting the introducer sheath therethrough, as well as "port access" types of procedures, which remotely access lumenal trees through ports and channels cut into the thorax of a patient, may also be suitable methods of introducing the devices and assemblies of the present invention into the targeted lumenal tree.

Specific embodiments and variations for device assemblies and methods of use have been described above by reference to the Figures. However, it is further contemplated that additional modifications to and combinations of the embodiments may be made by one of ordinary skill without departing from the scope of the present invention.

For example, a stent-graft assembly which is designed according to the embodiment shown and described by reference to FIG. 5 may be further combined with the embodiment shown and described by reference to FIGS. 8A–B. This additional combination of embodiments would therefore yield a "bifurcated stent-graft" which includes a lateral prosthesis body or stent extending from a first prosthesis body which is a stent-graft in the region of an aperture and side port through the first prosthesis body's graft member and stent, respectively. Moreover, still a further modification of this design may additionally provide another graft member onto the stent which forms the lateral prosthesis body, making that component also a stent-graft design in the overall combination "bifurcated stent-graft" assembly.

In another example which is not specifically shown or otherwise described above by reference to the Figures but which illustrates the broad scope of the present invention, the embodiment of FIG. 5 may also further be combined with that shown in FIG. 6, thereby resulting in a stent-graft according to FIG. 5 which includes an access device according to FIG. 6 which is engaged within the side port and aligned aperture of the stent and graft members of the assembly, respectively. Still further, combining the embodiment of FIG. 6 with that shown in FIG. 7 further results in a self-expanding stent embodiment with an access device engaged within the side port of the stent and also within a longitudinal groove of a radially confining sheath which is an expansion member for the stent assembly.

In addition, the present invention is further contemplated to include further modifications and combinations which have not been specifically herein described or shown as would be apparent to one of ordinary skill.

What is claimed is:

1. An endolumenal medical device assembly for engaging an interior surface of a body lumen wall at a bifurcation region of a body lumen, the bifurcation region including at least a first and a second branch lumen each having an entrance zone extending from a common branch lumen, comprising:

an expandable prosthesis having an elongate prosthesis body with a proximal end portion, a distal end portion, a length along a longitudinal axis extending between the proximal and distal end portions, a prosthesis passageway which extends along the length, and a plurality of side ports positioned along the length and through which the prosthesis passageway communicates externally of the elongate prosthesis body, the expandable prosthesis further being adjustable from a radially collapsed condition, wherein the elongate prosthesis body has a collapsed outer diameter, to a radially expanded condition, wherein the elongate prosthesis body has an expanded outer diameter which is larger than the collapsed outer diameter;

a delivery member having a proximal end portion and a distal end portion which is coupled to the expandable prosthesis, the delivery member being adapted to deliver the expandable prosthesis to the bifurcation region in a percutaneous translumenal procedure by manipulating the proximal end portion of the delivery member;

an expansion member with a proximal end portion and a distal end portion which is removably engaged with the elongate prosthesis body and adapted to be delivered by the delivery member, the distal end portion of the expansion member further being adapted to adjust the expandable prosthesis from the radially collapsed condition to the radially expanded condition when the elongate prosthesis body is engaged with the expansion member and is positioned at the bifurcation region; and a dilator with a proximal end portion and a distal end portion which is engaged within the prosthesis passageway and also within a selected one of the plurality of side ports when the expandable prosthesis is in the radially collapsed condition, wherein the distal end portion of the dilator is adjustable from a first dilator position, wherein the selected one of the plurality of side ports has an initial inner diameter, to a second dilator position, wherein the selected one of the plurality of side ports is dilated to an expanded inner diameter which is larger than the initial inner diameter.

2. The endolumenal medical device assembly of claim 1, wherein the expanded inner diameter approximates an inner lumenal diameter at the entrance zone of one of the first and second branch lumens.

3. The endolumenal medical device assembly of claim 1, wherein the expanded inner diameter is within the range of 1.0 to 5.0 millimeters.

4. The endolumenal medical device assembly of claim 1, wherein the dilator further comprises:

a dilator inflation lumen extending between the proximal and distal end portions of the dilator, the distal end portion of the dilator further including an expandable balloon which is fluidly coupled to the dilator inflation lumen and which is also engaged within the selected one of the plurality of side ports, the proximal end portion of the dilatory further including a fluid coupler which is in fluid communication with the dilatory inflation lumen, whereby the expandable balloon may be expanded from an unexpended condition, which characterizes the first dilatory position, to an expanded condition, which characterizes the second dilatory position.

5. The endolumenal medical device assembly of claim 4, wherein the dilator further comprises:

a guidewire with a proximal end portion and a distal end portion which is coupled to at least the distal end portion of the dilator, the distal end portion of the guidewire further including a shaped, radiopaque tip region which is steerable by torquing the proximal end portion of the guidewire.

6. The endolumenal medical device assembly of claim 4, wherein the dilator further comprises:

a guidewire tracking member extending at least along the distal end portion of the dilator, the guidewire tracking member further including a guidewire lumen which extends between a distal guidewire port located along the guidewire tracking member distally of the expandable balloon and a proximal guidewire port located along the guidewire tracking member proximally of the prosthesis passageway, the guidewire tracking member being adapted to track a guidewire slideably received within the guidewire lumen through the proximal and distal guidewire ports.

7. The endolumenal medical device assembly of claim 6, further comprising:

a guidewire which has a proximal end portion and a distal end portion with a shaped, radiopaque tip region which is steerable by torquing the proximal end portion of the guidewire, the distal end portion of the guidewire further being adapted to slideably engage within the guidewire lumen and through the proximal and distal guidewire ports.

8. The endolumenal medical device assembly of claim 1, wherein the dilatory further comprises:

a taper having a distally reducing outer diameter from a large outer diameter portion to a small outer diameter portion, wherein the first dilatory position the small outer diameter portion is engaged within the selected one of the plurality of side ports, and in the second dilatory position the large outer diameter portion is engaged within the side port.

9. The endolumenal medical device assembly of claim 1, wherein the expandable prosthesis further comprises an endolumenal stent which is adapted to provide radial support to the body lumen wall when the expandable prosthesis is expanded from the radially collapsed condition to the radially expanded condition.

10. The endolumenal medical device assembly of claim 9, wherein the endolumenal stent comprises a tubular stent wall which is formed by a plurality of integrated support members, the tubular stent wall further including a plurality of gaps formed between portions of the integrated support members, the side port being formed at least in part by one of the gaps.

11. The endolumenal medical device assembly of claim 1, wherein the expandable prosthesis is balloon expandable, and wherein the expansion member further comprises an inflation lumen extending between the proximal and distal end portions of the expansion member, the distal end portion of the expansion member further including an expandable balloon which is coupled to the inflation lumen and which is engaged within the prosthesis passageway, the proximal end portion of the expansion member further including a coupler which is coupled to the inflation lumen.

12. An endolumenal medical device assembly for engaging an interior surface of a body lumen wall at a bifurcation region of a body lumen, the bifurcation region including at least first and second branch lumens each having an entrance zone extending from a common branch lumen, comprising:

an expandable prosthesis having an elongate prosthesis body with a proximal end portion, a distal end portion, a length along a longitudinal axis extending between the proximal and distal end portions, a prosthesis passageway which extends along the length, and a plurality of side ports positioned along the length and through which the prosthesis passageway communicates externally of the elongate prosthesis body, the expandable prosthesis further being adjustable from a radially collapsed condition, wherein the elongate prosthesis body has a collapsed outer diameter, to a radially expanded condition, wherein the elongate prosthesis body has an expanded outer diameter which is larger than the collapsed outer diameter;

a delivery member having a proximal end portion and a distal end portion which is coupled to the expandable prosthesis, the delivery member further being adapted to deliver the expandable prosthesis to the bifurcation region in a percutaneous translumenal procedure by manipulating the proximal end portion of the delivery member;

an expansion member with a proximal end portion and a distal end portion which is removably engaged with the elongate prosthesis body and adapted to be delivered by the delivery member, the distal end portion of the expansion member further being adapted to actuate radial expansion of the expandable prosthesis from the radially collapsed condition to the radially expanded condition when the elongate prosthesis body is engaged with the expansion member and is positioned at the bifurcation region; and an access device with a proximal end portion and a distal end portion, the distal end portion of the access device being engaged within the prosthesis passageway at least along the proximal end portion of the expandable prosthesis and also within a selected one of said plurality of side ports when the expandable prosthesis is in both the radially collapsed and radially expanded conditions, whereby positioning the expandable prosthesis at the bifurcation region such that the distal end portion of the expandable prosthesis is located in the first branch lumen and the side port is aligned with the entrance zone to the second branch lumen, the access device is adapted to provide percutaneous translumenal access to the second branch lumen.

13. The endolumenal medical device assembly of claim 12, wherein the access device further comprises a guidewire which has a proximal end portion and a distal end portion with a shaped, radiopaque tip region which is steerable by torquing the proximal end portion of the guidewire, the distal end portion of the guidewire being engaged within the prosthesis passageway and extending distally through the side port when the expandable prosthesis is in both the radially collapsed and the radially expanded conditions.

14. The endolumenal medical device assembly of claim 12, wherein the access device further comprises:

a guidewire tracking member with a proximal end portion, a distal end portion which is engaged within the prosthesis passageway and when the expandable prosthesis is in both the radially collapsed and the radially expanded conditions, and a guidewire lumen which is formed at least in part by the distal end portion of the guidewire tracking member, the guidewire lumen communicating externally of the guidewire tracking member through a distal guidewire port located along the distal end portion of the guidewire tracking member at or adjacent to the side port and also through a proximal guidewire port located along the guidewire tracking member proximally of the prosthesis passageway, the guidewire tracking member further being adapted to track over a guidewire slideably received within the guidewire lumen through the proximal and distal guidewire ports.

15. The endolumenal medical device assembly of claim 14, further comprising:

a guidewire which has a proximal end portion and a distal end portion with a shaped, radiopaque tip region that is steerable by torquing the proximal end portion of the guidewire, the distal end portion of the guidewire further being adapted to slideably engage the guidewire tracking member within the guidewire lumen and through the proximal and distal guidewire ports.

16. The endolumenal medical device assembly of claim 12, wherein the expandable prosthesis further comprises:

an endolumenal stent which is adapted to provide radial support to the body lumen wall when the expandable prosthesis is expanded from the radially collapsed condition to the radially expanded condition.

17. The endolumenal medical device assembly of claim 16, wherein the endolumenal stent further comprises a tubular stent wall which is formed by a plurality of integrated support members, the tubular stent wall further including a plurality of gaps each being formed by a separation between at least a portion of adjacent integrated support members, the selected one of the plurality of side ports being formed at least in part by one of the gaps.

18. The endolumenal medical device assembly of claim 12, wherein the expandable prosthesis is balloon expandable, and wherein the expansion member further comprises an expansion member inflation lumen extending between the proximal and distal end portions of the expansion member, the distal end portion of the expansion member further including an expandable balloon which is coupled to the expandable member inflation lumen and which is engaged within the prosthesis passageway, the proximal end portion of the expansion member further including a coupler which is coupled to the expansion member inflation lumen.

* * * * *